(12) United States Patent
Hammerschmid et al.

(10) Patent No.: US 10,094,790 B2
(45) Date of Patent: Oct. 9, 2018

(54) MEASUREMENT CHAMBER FOR A COMPACT GONIOMETER IN AN X-RAY SPECTROMETER

(71) Applicant: Bruker AXS GmbH, Karlsruhe (DE)

(72) Inventors: Gerhard Hammerschmid, Karlsruhe (DE); Carolin Benz, Malsch (DE); Frank Filsinger, Karlsruhe (DE)

( * ) Notice: Subject to any disclaimer, the term of this patent is extended or adjusted under 35 U.S.C. 154(b) by 0 days.

(21) Appl. No.: 15/617,154

(22) Filed: Jun. 8, 2017

(65) Prior Publication Data
US 2017/0356862 A1    Dec. 14, 2017

(30) Foreign Application Priority Data

Jun. 10, 2016   (DE) .................. 10 2016 210 304

(51) Int. Cl.
*G01N 23/20*     (2018.01)
*G01N 23/207*    (2018.01)
(Continued)

(52) U.S. Cl.
CPC ... *G01N 23/2076* (2013.01); *G01N 23/20016* (2013.01); *G01N 23/223* (2013.01); *G01N 23/2209* (2018.02); *G01N 2223/076* (2013.01)

(58) Field of Classification Search
CPC ......... G01N 23/2076; G01N 23/20016; G01N 23/223; G01N 2223/076; G01N 23/2209
See application file for complete search history.

(56) References Cited

U.S. PATENT DOCUMENTS 4,417,355 A * 11/1983 Anisovich ............ G01N 23/207
                                                  378/49
6,233,307 B1 * 5/2001 Golenhofen ......... G01N 23/207
                                                  378/44
(Continued)

FOREIGN PATENT DOCUMENTS

EP         0597668 A1     5/1994
EP         0955539 A2    11/1999
(Continued)

OTHER PUBLICATIONS

The Rigaku Journal, Fluorescence X-ray Spectrometer System ZSX Series, vol. 16, No. 2, 1999.
(Continued)

*Primary Examiner* — Courtney Thomas
(74) *Attorney, Agent, or Firm* — Benoit & Côté Inc.

(57) ABSTRACT

A measurement chamber of an x-ray spectrometer for analyzing x-ray fluorescence radiation from a measuring sample has an entrance opening for the entry of x-ray fluorescence radiation into the measurement chamber, a first goniometer arm for holding and adjusting an analyzer crystal, and a second goniometer arm for holding and adjusting an x-ray detector. The measurement chamber and entrance opening are sealed in a vacuum-tight manner by way of a window. The chamber contains a bearing block for receiving and holding both goniometer arms in a concentric and rotatable manner, the arms each being mechanically adjustable by means of a piezo-motor, which is securely connected to the bearing block or a drive plate of the respective goniometer arm. The measurement chamber contains all mechanical components of the goniometer and allows for a more compact, lighter and more stable x-ray spectrometer with a rotatable goniometer and little heat influx into the system.

15 Claims, 4 Drawing Sheets

(51) Int. Cl.
    *G01N 23/20016*    (2018.01)
    *G01N 23/223*        (2006.01)
    *G01N 23/2209*     (2018.01)

(56) References Cited

U.S. PATENT DOCUMENTS

| | | |
|---|---|---|
| 6,292,532 B1 | 9/2001 | Kawahara et al. |
| 6,564,069 B1 | 5/2003 | Ishida |
| 9,008,272 B2 | 4/2015 | Shu et al. |

FOREIGN PATENT DOCUMENTS

| | | |
|---|---|---|
| JP | S6453144 A | 3/1989 |
| JP | H239150 | 3/1990 |
| JP | 2000249667 A | 9/2000 |
| JP | 2002311199 A2 | 10/2002 |
| WO | 9108471 A1 | 6/1991 |

OTHER PUBLICATIONS

Bruker, "S8 Tiger", bruker.com [online], Available from: (https://www.bruker.com/products/x-ray-diffraction-and-elemental-analysis/x-ray-fluorescence/s8-tiger-series-1/technical-details.html), [Accessed Jun. 1, 2017].

Gohshi et al., "Wide Range Two-crystal Vacuum X-ray Spectrometer for Chemical State Analysis", Applied Spectroscopy, Mar. 1, 1982.

\* cited by examiner

MEASUREMENT CHAMBER FOR A COMPACT GONIOMETER IN AN X-RAY SPECTROMETER

The invention relates to a measurement chamber for an x-ray spectrometer comprising a goniometer for analyzing x-ray fluorescence radiation emanating from a measuring sample to be examined that is irradiated by x-ray radiation, comprising an entrance opening for the entry of x-ray fluorescence radiation into the measurement chamber, a first goniometer arm for holding and adjusting an analyzer crystal, and a second goniometer arm for holding and adjusting an x-ray detector, wherein the measurement chamber has a vacuum-tight configuration and wherein the entrance opening for the x-ray fluorescence radiation is sealed in a vacuum-tight manner by way of a window.

An x-ray spectrometer and a measurement chamber having these features are known from "The Rigaku Journal, Vol. 16, number 2, 1999".

BACKGROUND OF THE INVENTION

X-ray fluorescence analysis (XRF analysis) is a powerful analytical method for detecting and characterizing very different materials. Depending on the analytic problem, different variants of XRF analysis are used; these differ in terms of the measurement geometry. An important variant that is used very frequently is the wavelength-dispersive XRF analysis, which uses the Bragg condition for analyzing the x-ray radiation.

The Bragg condition is a fundamental law of physics, which is applied for measuring the photon energy of x-ray radiation. If such radiation is diffracted at a crystal lattice, the following relationship applies between crystal and radiation parameters: $\lambda = 2d \cdot \sin \vartheta$ $\lambda$: wavelength of the radiation
2d-value: lattice plane distance of the crystal (property of the lattice structure)
$\vartheta$: angle of reflection with respect to the crystal lattice plane Here, x-ray spectrometers for wavelength-dispersive XRF analysis, as a rule, have a measurement chamber with a goniometer.

Goniometers according to the prior art require rotational movements that are matched to one another of two coaxial axes, namely for a crystal and for a detector unit, such that the Bragg condition is satisfied in a reproducible manner between the active crystal (or a multilayer) and the detector system. In order to be able to analyze different wavelength regions, crystal changers with a plurality of crystals, which are adjustable in a motor driven or manual manner such that they may be set into a working position, are also used in such designs.

Here, important boundary conditions are the following:

A high accuracy is required. This relates, in particular, to the angular position of the two spindles of the arms of the goniometer relative to one another and to the spatial orientation of the spindles relative to the x-ray-optical components, such as e.g. masks and collimators, but also, for example, relative to the crystal surface.

The effects of deformations of the measurement chamber, which is strained after the evacuation by the pressure difference between the varying atmospheric pressure and the vacuum in the measurement chamber, on the geometry of the beam path must be limited by structural means.

In respect of miniaturizing the overall appliances, a light compact, but nevertheless torsionally rigid construction is particularly important.

Thermal influxes of the goniometer and temperature variations in the measurement chamber should be as low as possible. By way of example, this has negative effects on the analyzer crystal. An important analyzer crystal consists of pentaerythritol (PET), which has a very pronounced coefficient of thermal expansion. There is a correspondingly pronounced change in the 2d value of the crystal structure in the case of temperature variations, as a result of which there is also a corresponding change in the reflection angle $\vartheta$ for x-ray radiation at a wavelength $\lambda$. Therefore, pronounced temperature variations lead to an incorrect measurement result.

Since an accurate measurement of the intensities in the case of low-energy x-rays, such as e.g. x-ray fluorescence radiation of light elements, is not possible in air because the x-rays are absorbed or scattered too strongly by gases in the air, such goniometers can only be housed in a vacuum chamber. As a result of the pressure difference between the varying atmospheric pressure and the vacuum, known apparatuses are complicated and, in particular, designed with thick walls in order to ensure the stability of the beam paths.

In an x-ray spectrometer, an x-ray source irradiates the sample to be analyzed. The x-ray fluorescence emitted by the sample enters into the evacuated measurement chamber, is incident on an analyzer crystal and reflected onto an x-ray detector from the latter. The crystal and detector are placed by means of a goniometer in such a way that the Bragg condition is satisfied for the wavelength to be analyzed.

Conventional goniometers typically contain stepper motors or servomotors which drive the spindles of the goniometer by means of appropriate gearing. Since the beam paths of an XRF goniometer must lie in a vacuum, two fundamental options emerge for such conventional drive concepts:

1. Motors Outside of the Vacuum Chamber

Here, the gearing mechanism may be housed within the vacuum chamber. However, to this end, only a small selection of greases are available for the gearing mechanism on account of the vacuum conditions and heat that arises in the gearing mechanism can only be dissipated poorly, which in turn leads to interferences from the set up in the vacuum chamber. However, the gearing mechanism may also lie outside of the vacuum chamber—like in the case of the Bruker S8 Tiger, published at https://www.bruker.com/de/products/x-ray-diffraction-and-elemental-analysis/x-ray-fluorescence/s8-tiger/technical-details.html. However, a disadvantage in that case is that a large opening is required for the passage of the shaft into the vacuum chamber, said large opening receiving rotatable parts and, at the same time, needing to be vacuum tight. Consequently, a massive structure of the gearing mechanism holder, and hence of the wall of the measurement chamber, is required on account of the pressure difference.

2. Motors within the Vacuum Chamber

However, it is desirable to attach the motors within the vacuum chamber in order to avoid massive setups for the vacuum passage and improve the vacuum tightness. Here too, the heat dissipation by way of thermal radiation is poor. Cooling can only be achieved by complicated measures, such as e.g. water cooling or the like.

Thermal Power Losses During Static Holding of a Position:

Motors for goniometers are usually designed as stepper motors which are actuated within the scope of micro-step operation in order to improve the resolution. In this mode, the motor phases must permanently be supplied with a power at a specific ratio in order not to fall back to the next full step of the stator.

This property is independent of the connected gearing mechanism type. As a result, electric power is converted into heat within the vacuum chamber.

Servomotors must likewise be permanently supplied with power in order to hold a non-balanced spindle in a static position. This also applies to specific direct drives, which act without a gearing mechanism directly onto the goniometer spindles.

The use of piezo-motors for goniometers for x-ray diffractometers is known from JP 2002 311199 A, but not for applications in conjunction with a vacuum housing for the measurement chamber for the purposes of analyzing x-ray fluorescence radiation as in the case of a generic x-ray spectrometer. In JP 2002 311199 A, two ring-shaped piezo-motors are described in a horizontal geometry for driving two coaxial shafts. The piezo-motors have been installed in symmetric fashion and have the same dimensions. U.S. Pat. No. 9,008,272 B2 also exhibits an x-ray spectrometer with movable arms that are adjustable by piezo-motors.

OBJECT OF THE INVENTION

By contrast, the present invention is based on the object of providing an x-ray spectrometer that is more compact, lighter and more stable when compared to the prior art, comprising a rotatable goniometer of the type defined at the outset for the purposes of analyzing x-ray fluorescence radiation, which causes a heat influx into the overall system that is as low as possible. At the same time, the mechanical stability requirements in respect of the measurement chamber should be optimized in such a way that costs and weight are reduced.

BRIEF DESCRIPTION OF THE INVENTION

This object is achieved by virtue of the measurement chamber containing a bearing block for receiving and holding both goniometer arms in a concentric and rotatable manner, and respectively one drive plate per goniometer arm, said drive plates being movable relative to the bearing block, by virtue of the goniometer arms each being mechanically adjustable by means of a piezo-motor, which is securely connected to the bearing block or a drive plate of the respective goniometer arm, and by virtue of the measurement chamber containing all mechanical components of the goniometer.

Principle of Operation of the Invention and Further Advantages in Relation to the Prior Art Thus, the present invention proposes a measurement chamber for an x-ray goniometer, which facilitates a higher stability and more compact structure of the x-ray spectrometer and a lower heat influx.

The use of piezo-motors in conjunction with the bearing block brings about, overall, a higher stability and more compact structure of the x-ray spectrometer. Piezo-motors produce less heat than conventional motors, both in adjustment operation and in holding operation, and, as a rule, have a smaller embodiment. In the holding operation, the increased frictional force between the piezo-motor and the counter face on the goniometer arm, in particular, is advantageous. In the case of a suitable design, no holding current is required for the holding operation. The reduced heat influx in turn leads to smaller deformations of the measurement arrangement. Holding both goniometer arms in a manner that is largely decoupled from the walls of the measurement chamber likewise increases the stability of the measurement arrangement since forces acting via the vacuum onto the walls do not directly influence the position of the goniometer, as in the case of conventional vacuum spectrometers comprising a vacuum passage for the spindles of the goniometer arms. Moreover, it is easier to configure the measurement chamber in a vacuum-tight manner because it contains all mechanical components of the goniometer.

PREFERRED EMBODIMENTS OF THE INVENTION

Embodiments of the invention, in which the measurement chamber has a holding wall that is designed to be thicker in relation to the side and cover walls and that comprises the entrance opening, the bearing block being securely connected to said holding wall, are particularly preferred. Then, only one wall of the measurement chamber needs to have a torsionally rigid embodiment and needs to be processed accurately. The remaining walls are no longer relevant to the beam path, and so thinner wall thicknesses and lower demands on the accuracy are possible. This, in particular, also contributes to saving weight and costs. Moreover, the influence of the deformation of this holding wall on the measurement arrangement is lower because the bearing block is oriented along the entry direction of the x-ray fluorescence radiation. By way of example, if the holding wall deforms inwardly, this does not lead to a change in the angle of incidence on the analyzer crystal.

Further advantageous embodiments are characterized in that the drive plate of the goniometer arm for the detector and the drive plate of the goniometer arm for the analyzer crystal are situated on different sides of the bearing block. This facilitates an even more compact structure, in particular also a reduction in the installation depth and a better force equilibrium during operation of the arrangement.

Similar advantages can also be obtained in embodiments in which the analyzer crystal is situated on the side of the bearing block that lies opposite to the drive plate of the goniometer arm for the analyzer crystal.

It may also be expedient for use if, in the case of the measurement chamber according to the invention, the piezo-motors are securely connected to the bearing block and arranged in such a way that they may act on the drive plates of the goniometer arms from the same side. Then, access is only required from one side of the goniometer when servicing the goniometer and the motors.

Particularly preferred variants of the invention in one class of embodiments are distinguished by the goniometer arms and the drive plates being designed in such a way that, when the measurement chamber is open, the piezo-motors can be removed or assembled without the removal of further components of the goniometer. This simplifies servicing and leads to savings in terms of time and costs. Optionally, to this end, the goniometer arms should be driven into a servicing position.

A further advantageous embodiment of the measurement chamber according to the invention is distinguished by the piezo-motors and the sensor for an encoder for recognizing the rotational position of the goniometer arms being fastened separately to the bearing block. As a result, servicing of the piezo-motor has no influence—in any case, no negative influence—on the calibration of the angle measurement.

An embodiment of the invention in which balancing weights for the goniometer arms are also provided is particularly preferred, said balancing weights bringing the center of gravity of the goniometer arm and the moving attachments up to a few millimeters, preferably up to approximately 2 mm, from the respective axis of rotation. As a result of this, it is possible to minimize the contact pressure of the piezo-motors to the tracks, said contact pressure being required for holding a position, as a result of which the accuracy and uniformity of the movement is increased. An additional transportation protection for the mechanism can be dispensed with and the appliance is immediately ready for use at the customer.

A further advantageous embodiment of the invention is distinguished by the piezo-motors having a gearing-mechanism-free design and being equipped with an electronic regulating device for positioning the goniometer arms. This precludes mechanical power loss in the gearing mechanism, leading to an even lower thermal influx. Moreover, there are no negative effects of gearing mechanism errors, possible transmission errors or back lash on the positioning of the arrangement.

A class of embodiments of the measurement chamber according to the invention, in which the goniometer arms or the bearing block comprise tracks made of a hard, preferably hardened, material, in particular metal or ceramics, for the contact to the piezo-motors, are very particularly preferred, in which as well the radius for the track of the goniometer arm for the x-ray detector is smaller than the radius for the track of the goniometer arm for the analyzer crystal, wherein the ratio of the radii lies between 0.25-0.75. As a rule, wear occurs on the plastic contact finger of the piezo-motor, which is usually designed to be softer, in particular containing plastic. As a result of the lower hardness of the contact finger, wear tends to occur on same. Since it can be replaced more easily, this yields savings in terms of time and costs during servicing.

Furthermore, it is advantageous that there may be an optimized adaptation of the requirements to the angular accuracy and the exactly required angular speed in the case of different radii. In general, the detector unit should preferably be driven at twice the speed, but it requires a lower angular accuracy than the analyzer crystal. According to the invention, a better accuracy is achieved solely by the different radii in the case of the same travel of the piezo-motors.

Advantageous developments of this class of embodiments are characterized in that the tracks are arranged on the goniometer arms in a radially outer region in relation to the axis of rotation of the goniometer arms. A high angular resolution of the motor-driven drives is achieved as a result.

Particularly preferred variants of this class of embodiments are distinguished by the tracks each having one, preferably only one, segment-shaped, in particular annular-segment-shaped section. This measure also facilitates a more compact structure. On account of the type of the employed design of the measurement chamber, the track may be restricted to an expedient angular range. A complete 360° rotation of the goniometer arms is not mandatory. Usually, a measurement with the detector in the angular range 0-180° suffices. Accordingly, the angular range of the segments can be adapted, wherein the angular range of the track for the analyzer crystal may be embodied to be smaller than the angular range for the x-ray detector since the latter must always pass through twice the angle in the case of a change in angle of the analyzer crystal.

Advantageously, the angular range for the analyzer crystal can be restricted up to 90° and the angular range for the x-ray detector can be restricted to less than 180°.

A further class of particularly preferred embodiments of the measurement chamber according to the invention is distinguished by encoder strips for ascertaining the exact current angular position of the goniometer arms being attached to the goniometer arms. These strips facilitate a direct angle measurement on the component to be moved, and so wear of the drives has no influence on the angle measurement. Moreover, this dispenses with a bothersome running-in behavior by heating since it is always possible to ascertain the absolute position of the goniometer arms. The encoder strips are advantageously read by a readout unit which is assembled next to the piezo-motor in each case.

A development of this class of embodiments that is particularly simple to realize provides for the encoder strips to be bent in a circular or circular-segment-shaped manner. This results in an ideal form for an angle measurement. Advantageously, such encoder strips are attached to a likewise circularly bent section of a goniometer arm, in particular at the end side of the drive plate.

Further advantages of the invention emerge from the description and the drawing.

The shown and described embodiments should not be understood to be a comprehensive list but, instead, have an exemplary character for explaining the invention.

DETAILED DESCRIPTION OF THE INVENTION AND DRAWING

The invention is illustrated in the drawing and explained in more detail on the basis of exemplary embodiments. In the figures.

Basic Design of the Piezo-Goniometer According to the Invention the goniometer consists of the following principal components:
  A bearing block with drives and position sensors
  Two concentric ball bearings for the two spindles
  A spindle for the crystal changer unit, designed as follows:
    A central shaft through the bearing block
    The crystal changer for automatically selecting different analyzer crystals is situated on one side of the bearing block. All of the other optical components of the beam path are also situated on this side of the bearing block. The geometric axis of rotation lies exactly in the plane of the active crystal surface On the other side of the bearing block there is a drive plate comprising:

A track for the associated piezo-motor

Encoder strips, applied in a circularly bent manner

Balancing weights in order to bring the center of gravity of the spindle and moving attachments up to a few millimeters (in this case approximately 2 mm) from the axis of rotation A spindle for moving the detector systems. It is designed as follows:

The mechanical bearing is arranged in a ring-shaped manner about the axis of rotation for the crystal changer unit.

There is no separate shaft through the bearing block. The moving drive plate for detector unit, track and encoding strips is situated directly on the bearing ring and likewise carries balancing weights in order to bring the center of gravity of the spindle and moving attachments up to a few millimeters (in this case approximately 3.5 mm) from the axis of rotation.

All mechanical components of the goniometer
  are situated within the vacuum chamber (measurement chamber)
  are fastened to a compact narrow bearing block which is connected to the chamber on the beam entrance side.

Type of drive:
  piezo-motors (without a gearing mechanism) with a control loop for positioning purposes.
  Position monitoring by an angle encoder directly on the spindle.

What is advantageous for implementing the present concept of the invention is that the carrier plates, at least to a great extent, tracks and encoder strips of the goniometer are embodied as circular segments. The spatial requirements in the vacuum chamber can be minimized by this embodiment. Here, the circular segments of the tracks and encoders are oriented in such a way that the axis of rotation lies as closely as possible to the input collimator for the beam entrance in the bearing block, despite large radii.

Figure 1:
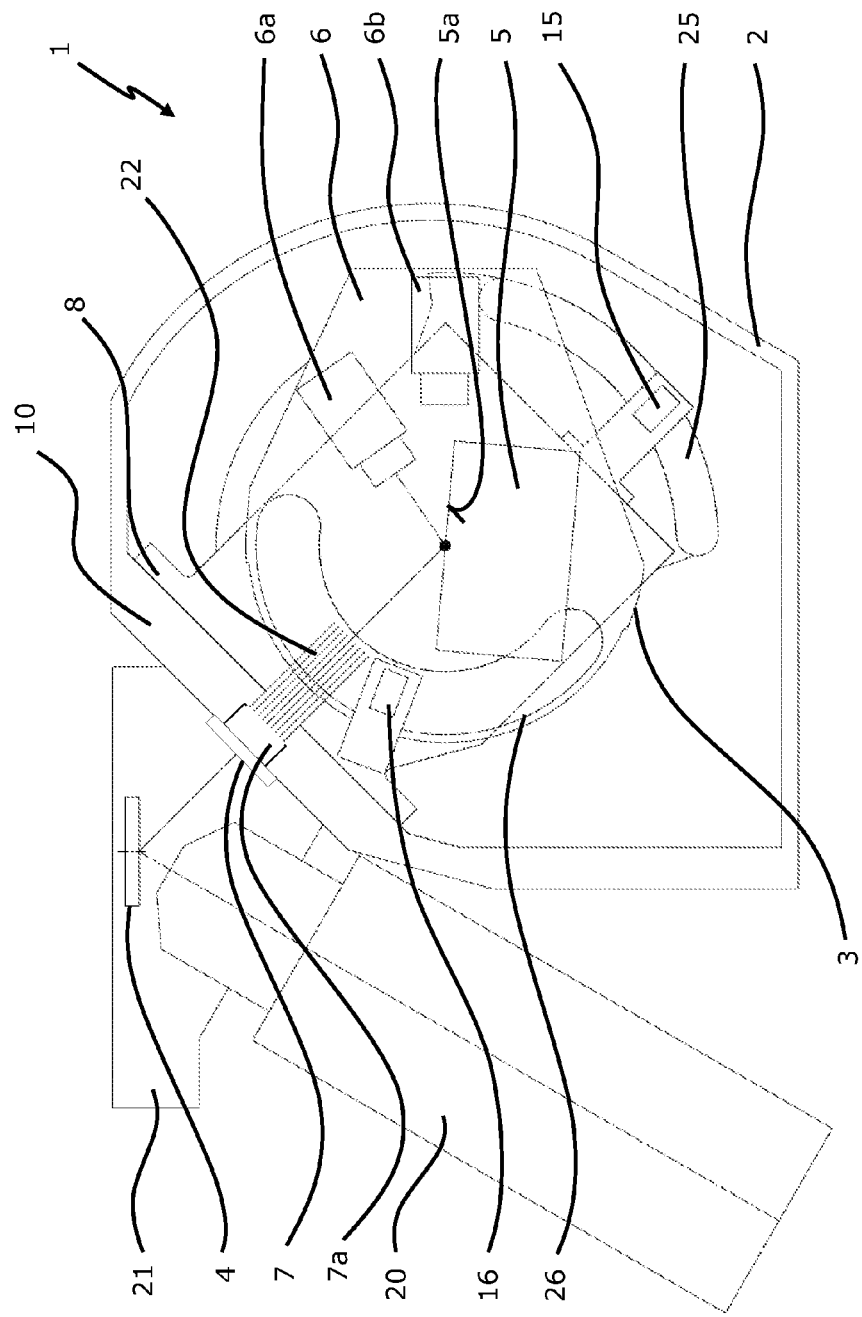
FIG. 1 shows the schematic design of an x-ray spectrometer with a measurement chamber according to the invention in a side view.

FIG. 1 schematically illustrates the overall design of an x-ray spectrometer 1 with a measurement chamber 2 according to the invention, the latter comprising a goniometer 3. The x-ray spectrometer 1 serves to analyze x-ray fluorescence radiation, which emanates from a measuring sample 4 to be examined that is irradiated by x-ray radiation. The measurement chamber 2 comprises an entrance opening 7a for x-ray fluorescence radiation to enter into the measurement chamber, a first goniometer arm 5 for holding and adjusting an analyzer crystal 5a with a crystal changer 5', and a second goniometer arm 6 for holding and adjusting an x-ray detector 6a, 6b, with the measurement chamber 2 having a vacuum-tight configuration and the entrance opening 7a for the x-ray fluorescence radiation being sealed in a vacuum-tight manner by a window 7.

The x-ray spectrometer 1 comprises an x-ray source 20 and a sample chamber 21. A collimator 22 is arranged downstream of the window 7 of the measurement chamber 2.

The measurement chamber 2 according to the invention is distinguished by containing a bearing block 8 for concentrically and rotatably receiving and holding the two goniometer arms 5, 6 which are respectively mechanically adjustable by means of a piezo-motor 15, 16, which is securely connected to the bearing block 8 or a drive plate 9', 9" of the respective goniometer arm 5, 6, and all mechanical components of the goniometer 3.

The x-ray spectrometer is arranged vertically in FIG. 1. As a result, the measuring sample 4 has a horizontal orientation, which simplifies the measurement of liquids in sample containers.

The measurement chamber 2 has a holding wall 10 comprising the entrance opening, said holding wall having a thicker design than the side and cover walls and being securely connected to the bearing block 8 (see FIG. 1).

The piezo-motors 15, 16 are securely connected to the bearing block 8 and arranged in such a way that they may act on the drive plates 9', 9" of the goniometer arms 5, 6 from the same side. In the shown embodiment, the first goniometer arm in this case comprises all movable parts in conjunction with the analyzer crystal and, in particular, passes through the bearing in the bearing block. By contrast, the second goniometer arm comprises the parts that are moved together with the detectors. In the shown embodiment, this arm is held in the bearing block by a ball bearing (see FIG. 2b). Moreover, the piezo-motors 15, 16 have a gearing-mechanism-free design and are equipped with an electronic regulating device for positioning the goniometer arms 5, 6. The goniometer arms 5, 6 and the drive plates 9', 9" are designed in such a way that, in the case of an opened measurement chamber 2, the piezo-motors 15, 16 can be removed or assembled without removing further components of the goniometer 3. In order to prevent the piezo-motor 15 for the analyzer crystal from being covered by the drive plate 9", the goniometer arms are intended to be driven into a servicing position to this end.

The goniometer arms 5, 6 or the bearing block 8 comprise tracks 25, 26 for the contact to the piezo-motors 15, 16, said tracks being made of a hard, preferably hardened, material, in particular a metal or ceramic. The radius for the track 26 of the second goniometer arm 6 is smaller than the radius for the track 25 of the first goniometer arm 5, wherein the ratio of the two radii lies between 0.25 and 0.75. The tracks 25, 26 are arranged on the goniometer arms 5, 6 in a radially outer region in relation to the axis of rotation of the goniometer arms 5, 6 and each have one, preferably only one, segment-shaped, in particular annular-segment-shaped section.

Figure 2:
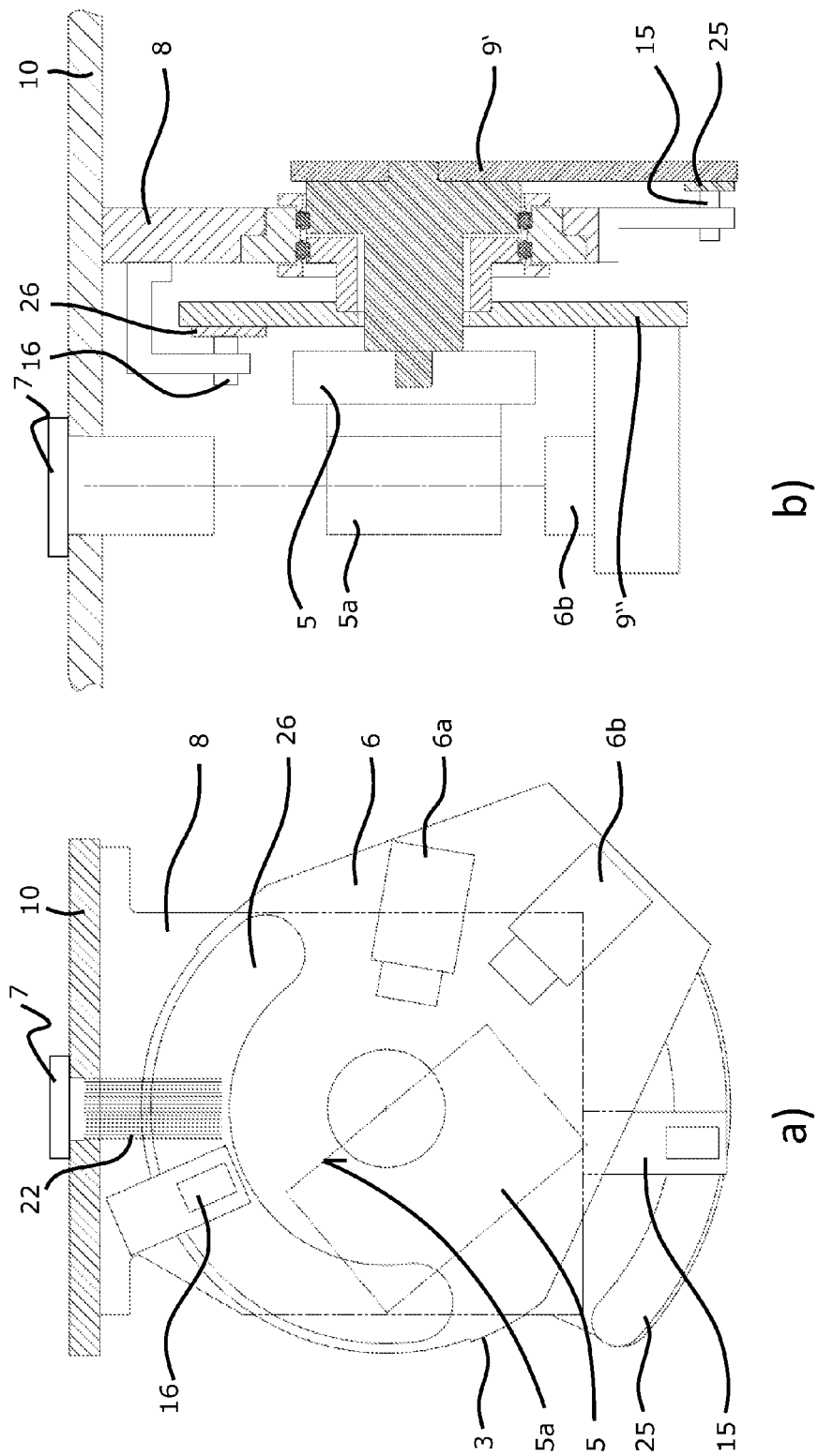
FIG. 2 shows a schematic illustration of an embodiment of the piezo-goniometer system according to the invention,
  a) in a side view, which is rotated in comparison with FIG. 1,
  b) in a sectional view, with the sectional plane being spanned by the entry direction of the x-ray beam and the axis of rotation of the goniometer.

FIGS. 2a and 2b schematically illustrate an embodiment of the piezo-goniometer system according to the invention. FIG. 2a shows a side view of the goniometer without a measurement chamber, which is depicted in a rotated manner in comparison with FIG. 1 such that the radiation is incident perpendicularly from the top in this case. FIG. 2b shows a section through the goniometer for elucidating the spatial arrangement of the goniometer arms, the piezo-motors, tracks and drive plates.

The analyzer crystal 5a and the drive plate 9' thereof are arranged on opposite sides of the bearing block 8. The drive plate 9' of the first goniometer arm 5 and the drive plate 9" of the second goniometer arm 6 are likewise arranged on opposite sides of the bearing block 8 (see also FIG. 2b).

Figure 3:
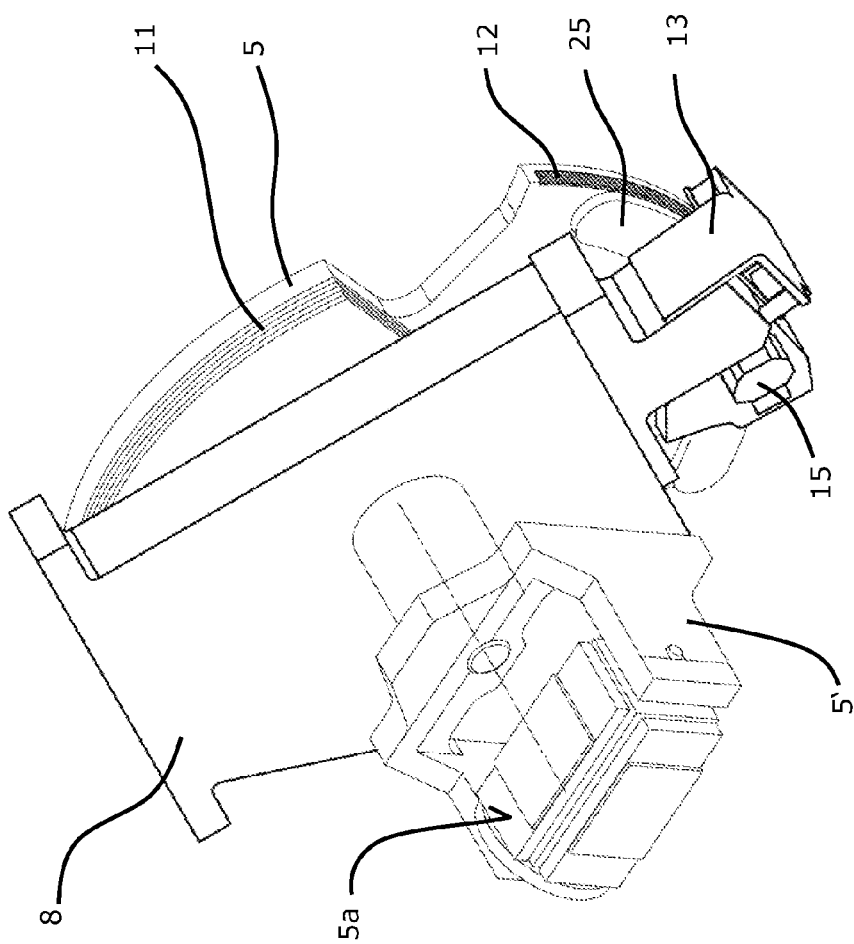
FIG. 3 shows a schematic spatial plan view from obliquely above onto an embodiment of a goniometer arm according to the invention, in this case for the analyzer crystal.

FIG. 3 shows the bearing block 8 (with the thick lines) and the goniometer arm 5 for the crystal changer unit in detail. The rotating components are depicted using thin lines. The crystal changer 5' is situated in front of the bearing block 8; the drive plate with the encoder tape 12, the track 25 and the counterweights 11 is situated behind the bearing block 8. The motor holder, the piezo-motor 15 and the readout unit 13 of the encoder are fastened to the bearing block 8 that is statically fixed on the chamber wall 10. The spindle is mounted in the bearing block 8 and passes through the latter. The drive plate with encoder strips 12, track 25 of the drive 15 and balancing weights 11 is securely connected to the spindle and lies behind the bearing block 8. The crystal changer 5' is likewise securely connected to the spindle and lies in front of the bearing block 8.

Balancing weights 11 which bring the center of gravity of the spindle and moving attachments up to a few millimeters, preferably up to approximately 2 mm, from the axis of rotation are provided for the goniometer arms 5, 6 (see FIG. 3).

Circular or circular-segment-shaped bent encoder strips 12 for ascertaining the precise current angular position of the goniometer arms 5, 6 are attached to the goniometer arms 5, 6 (see FIG. 3). The piezo-motors 15, 16 and the sensors for the encoders are fastened separately to the bearing block 8. Electronic readout units 13 are provided for the encoders.

Figure 4:
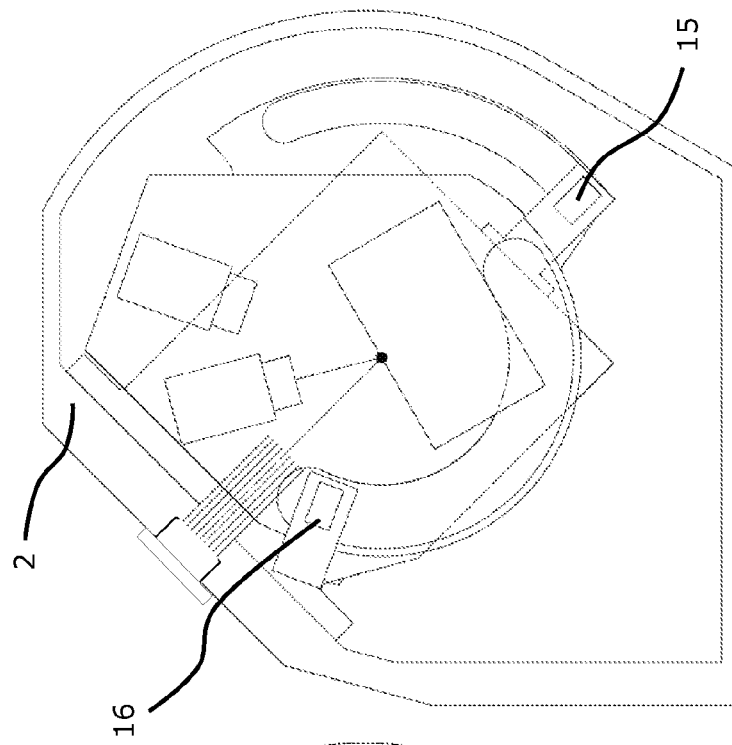
FIG. 4 shows a schematic side view of the overall design of an embodiment of the measurement chamber according to the invention for two different angular orientations of the goniometer arrangement, namely
  a) with a flat angle of incidence of the x-ray radiation with respect to the crystal surface
  b) with a steep angle of incidence of the x-ray radiation.
Figure 4:
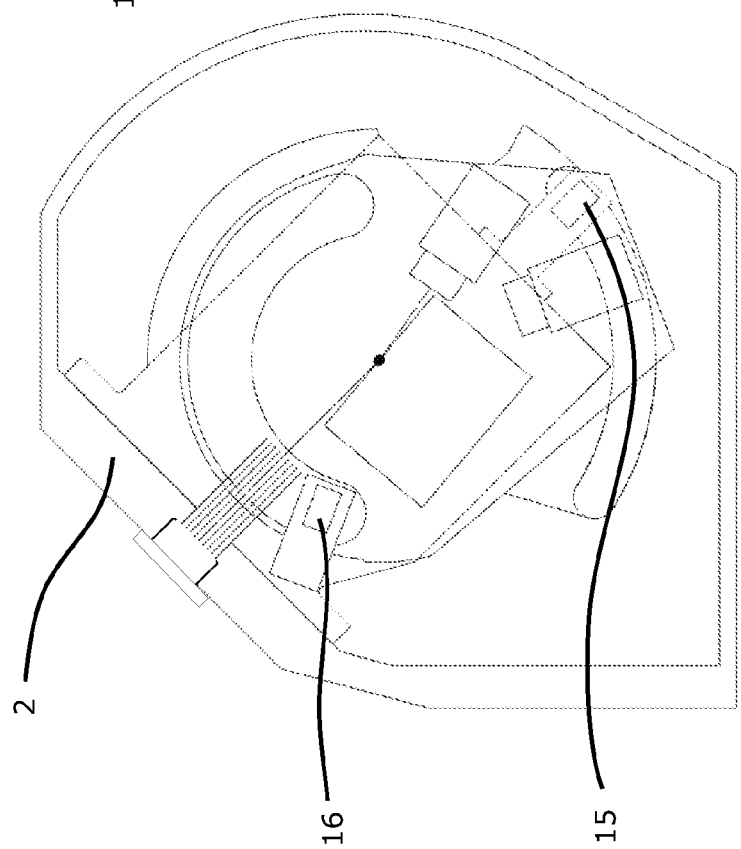

Finally, FIGS. 4a and 4b show, in a side view, the piezo-goniometer according to the invention in two measurement positions, namely with a flat angle of incidence of the x-ray radiation with respect to the crystal surface in FIG. 4a and with a steep angle of incidence in FIG. 4b. It can easily be recognized in the figures that the piezo-motor 15 for the crystal changer 5' is situated further to the outside with respect to the common axis of rotation than the piezo-motor 16 for the detector 6a. As a result, the detector 6a passes over a larger angular range or the analyzer crystal 5a receives a higher angular resolution in the case of the same number of steps. Also, the tracks 25, 26 for the two piezo-motors 15, 16 connected therewith that are embodied as annular segments can be identified. Both are designed for a restricted angular range, as a result of which the x-ray spectrometer 1 may be designed to be more compact.

As depicted in the figures, use is advantageously also made of two detectors 6a, 6b in the design. As a result of this, it is possible to use the ideal detector depending on the energy of the x-ray radiation to be measured.

The novel approach according to the invention for the goniometer with piezo-drives has the following advantages:
- Within the vacuum chamber, the compact bearing block of the goniometer is only supported on the side wall of the measurement chamber to which the sample chamber has also been flanged. All remaining walls need not maintain such an accurate geometric relationship with respect to the beam path and may therefore be designed to be thinner and less rigid in relation to pressure differences. The concept allows a significant reduction in weight of the measurement chamber.
- In the concept, the piezo-motors are affixed directly to the bearing block of the goniometer mount at short distances
  - Short distances permit a good heat dissipation by way of the holder despite the vacuum
  - Good rigidity with a low weight
- Compared with the BRUKER S8 TIGER, cited above, having a worm drive, the heat influx is significantly lower since there is no need for a mechanical gearing mechanism However, the mechanical design according to the invention also offers a few further advantages:
- Optimized working radii of the piezo-motors: the shaft with the crystal changer needs only to be displaced by half the angular path in relation to the shaft with the detector unit. At the same time, the crystals need to be moved with a better angular resolution, which, in the novel concept, is assisted by virtue of the working radius for the crystal changer drive being significantly larger than for the detector drive (but not exactly in the ratio 1:2). It is not easy to implement this approach: in contrast to the requirements on the working radii, the detector unit is situated further away from the spindle while the crystal changer is placed centrally in the vicinity of the spindle.
- If the measurement chamber is open, both piezo-motors can easily be removed from the front side of the goniometer block, without it being necessary to disassemble the entire unit from the measurement chamber. This significantly simplifies regular servicing work.

X-ray fluorescence analysis is the main field of application of the arrangement according to the invention.

LIST OF REFERENCE SIGNS

1 X-ray spectrometer
2 Measurement chamber
3 Goniometer
4 Measuring sample
5 First goniometer arm
5a Analyzer crystal
5' Crystal changer
6 Second goniometer arm
7 Window
7a Entrance opening
8 Bearing block
9' Drive plate of the first goniometer arm
9" Drive plate of the second goniometer arm
10 Holding wall
11 Balancing weights
12 Encoder strips
13 Readout unit for the encoder
15 Piezo-motor for the crystal changer
16 Piezo-motor for the detectors
20 X-ray source
21 Sample chamber
22 Collimator
25 Track of the first goniometer arm
26 Track of the second goniometer arm

The invention claimed is:

1. A measurement chamber (2) of an x-ray spectrometer (1) comprising a goniometer (3) for analyzing x-ray fluorescence radiation emanating from a measuring sample (4) to be examined that is irradiated by x-ray radiation, comprising
an entrance opening for the entry of x-ray fluorescence radiation into the measurement chamber (2),
a first goniometer arm (5) for holding and adjusting an analyzer crystal (5a), and
a second goniometer arm (6) for holding and adjusting an x-ray detector (6a, 6b),
wherein the measurement chamber (2) has a vacuum-tight configuration and wherein the entrance opening for the x-ray fluorescence radiation is sealed in a vacuum-tight manner by way of a window (7),
wherein the measurement chamber (2) contains a bearing block (8) for receiving and holding both goniometer arms (5, 6) in a concentric and rotatable manner, and respectively one drive plate (9', 9") per goniometer arm (5, 6), said drive plates being movable relative to the bearing block (8), wherein the goniometer arms (5, 6) are each mechanically adjustable by means of a piezo-motor (15, 16), which is securely connected to the bearing block (8) or a drive plate (9', 9") of the respective goniometer arm (5, 6), and wherein the measurement chamber (2) contains all mechanical components of the goniometer (3).

2. The measurement chamber as claimed in claim 1, wherein the measurement chamber (2) has a holding wall (10) that is designed to be thicker in relation to the side and cover walls and that comprises the entrance opening, the bearing block (8) being securely connected to said holding wall.

3. The measurement chamber as claimed in claim 1, wherein the drive plate (9") of the second goniometer arm (6) and the drive plate (9') of the first goniometer arm (5) are arranged on different sides of the bearing block (8).

4. The measurement chamber as claimed in claim 1, wherein the analyzer crystal (5a) is arranged on the side of the bearing block (8) that lies opposite to the drive plate (9') of the first goniometer arm (5).

5. The measurement chamber as claimed in claim 1, wherein the piezo-motors (15, 16) are securely connected to the bearing block (8) and arranged in such a way that they may act on the drive plates (9', 9") of the goniometer arms (5, 6) from the same side.

6. The measurement chamber as claimed in claim 1, wherein the goniometer arms (5, 6) and the drive plates (9', 9") are designed in such a way that, when the measurement chamber (2) is open, the piezo-motors (15, 16) can be removed or assembled without the removal of further components of the goniometer (3).

7. The measurement chamber as claimed in claim 1, wherein balancing weights (11) for the goniometer arms (5, 6) are present, said balancing weights bringing the center of gravity of the goniometer arm (5, 6) and the moving attachments up to a few millimeters, preferably up to approximately 2 mm, from the respective axis of rotation.

8. The measurement chamber as claimed in claim 1, wherein the piezo-motors (15, 16) have a gearing-mechanism free design and are equipped with an electronic regulating device for positioning the goniometer arms (5, 6).

9. The measurement chamber as claimed in claim 1, wherein the goniometer arms (5, 6) or the bearing block (8) comprise tracks (25, 26) made of a hard, preferably hardened, material, in particular metal or ceramics, for 5 the contact to the piezo-motors (15, 16), and wherein the radius for the track (26) of the second goniometer arm (6) is smaller than the radius for the track (25) of the first goniometer arm (5), wherein the ratio of the two radii lies between 0.25 and 0.75.

10. The measurement chamber as claimed in claim 9, wherein the tracks (25, 26) are arranged on the goniometer arms (5, 6) in a radially outer region in relation to the axis of rotation of the goniometer arms (5, 6).

11. The measurement chamber as claimed in claim 9, wherein the tracks (25, 26) each have one, preferably only one, segment-shaped, in particular annular-segment-shaped section.

12. The measurement chamber as claimed in claim 11, wherein the angular range for the analyzer crystal is restricted up to 90° and the angular range for the x-ray detector is restricted to less than 180°.

13. The measurement chamber as claimed in claim 1, wherein encoder strips (12) for ascertaining the exact current angular position of the goniometer arms (5, 6) are attached to the goniometer arms (5, 6).

14. The measurement chamber as claimed in claim 13, wherein the encoder strips (12) are bent in a circular or circular-segment-shaped manner.

15. The measurement chamber as claimed in claim 13, wherein the piezo-motors (15, 16) and the sensor for the encoder are fastened separately to the bearing block (8).

* * * * *